United States Patent [19]

Vu

[11] Patent Number: 4,842,850
[45] Date of Patent: Jun. 27, 1989

[54] HAIR CARE COMPOSITIONS

[75] Inventor: Hoang D. Vu, Cincinnati, Ohio

[73] Assignee: The Procter & Gamble Company, Cincinnati, Ohio

[21] Appl. No.: 51,548

[22] Filed: May 18, 1987

[51] Int. Cl.$^4$ .............................................. A61K 7/075
[52] U.S. Cl. .............................. 424/70; 252/DIG. 13; 252/554; 252/174.23
[58] Field of Search .................. 424/70; 252/555, 552, 252/554, DIG. 13

[56] References Cited

U.S. PATENT DOCUMENTS

| | | | |
|---|---|---|---|
| 3,325,439 | 6/1967 | Steinbach | 260/32.8 |
| 3,681,122 | 8/1972 | Domicone et al. | 117/124 |
| 4,559,227 | 12/1985 | Chandra et al. | 424/70 |
| 4,704,272 | 11/1987 | On et al. | 424/70 |
| 4,728,457 | 3/1988 | Fieler et al. | 252/DIG. 13 X |

FOREIGN PATENT DOCUMENTS

| | | |
|---|---|---|
| J6 1044-971-A | 3/1986 | Japan . |
| J6 1195-138-A | 8/1986 | Japan . |
| 2170216 | 7/1986 | United Kingdom ....... 252/DIG. 13 |

*Primary Examiner*—Ellis P. Robinson
*Assistant Examiner*—Susan S. Rucker
*Attorney, Agent, or Firm*—Douglas C. Mohl; Steven J. Goldstein; Richard C. Witte

[57] ABSTRACT

Shampoo compositions which give both improved style retention and hair conditioning properties are disclosed herein. The compositions comprise from about 0.01% to about 10% of a rigid silicone polymer premixed with a concentrated alkyl glyceryl sulfonate paste.

7 Claims, No Drawings

HAIR CARE COMPOSITIONS

TECHNICAL FIELD

The present invention relates to shampoo compositions which have improved hair conditioning and style retention properties due to the inclusion of particular types of silicone polymers which are premixed with a surfactant prior to addition to the total composition.

BACKGROUND OF THE INVENTION

The desire to have hair retain a particular shape is widely held. The two methodologies of accomplishing this are permanent chemical alteration of the hair or a temporary alteration. A temporary alteration is one which can be removed by water or by shampooing. This has generally been accomplished by means of the application of a separate composition to dampened hair, i.e., after shampooing and/or conditioning, and prior to drying and/or styling. The materials used to provide setting benefits have generally been resins or gums and have been applied in the form of mousses, gels, lotions, and sprays. However, some people desire a high level of style retention in a single composition such as that provided by a separate composition without the negative impact of these materials on dry hair properties, particularly ease of combing and hair feel. Silicones can provide such benefits.

Silicones in various hair care compositions have been disclosed in a large number of different publications, including U.S. Pat. Nos. 3,964,500, to Drakoff, issued June 22, 1976; 4,364,837, to Pader, issued Dec. 21, 1981; 4,341,799, to Good, issued July 27, 1982; 4,465,619, to Boskamp, issued Aug. 14, 1984; 4,515,784, to Bogartus, issued May 7, 1985; 4,387,090, to Bolich, issued June 7, 1983; 4,529,586, to DeMarco et al, issued July 16, 1985; and 4,559,227, to Chardia et al, issued Dec. 17, 1985.

It has now been discovered that shampoo compositions comprising certain rigid silicone polymers and volatile carriers provide increased style retention and hair condition. The compositions provide the increased style retention to the hair without decreasing dry hair properties such as ease of combing. This improved performance is obtained by mixing the rigid silicone with a surfactant prior to mixing with the other shampoo components.

It is, therefore, an object of the present invention to provide shampoo compositions which contain a high molecular weight rigid silicone polymer dispersed in a surfactant paste premix prior to mixing with other shampoo components.

It is a further object of the present invention to provide stable shampoo compositions containing a volatile carrier.

It is a further object of the present invention to provide shampoo compositions providing good style retention.

It is a further object of the present invention to provide an improved method of temporarily styling and conditioning hair.

It is a further object of the present invention to provide a method of treating hair for improved style retention.

These and other objects will become readily apparent from the detailed description which follows.

Unless otherwise indicated, all percentages and ratios herein are by weight.

SUMMARY OF THE INVENTION

The present invention relates to hair care compositions comprising from about 0.01% to about 10% of a rigid silicone polymer, from about 0.1% to about 10% of a volatile carrier, from about 10% to about 35% of a synthetic surfactant, from about 0.2% to about 12% of about a 50% aqueous solution of alkyl glyceryl sulfonate, and water, wherein the rigid silicone is mixed with the sulfonate solution prior to mixing with the other shampoo component.

DETAILED DESCRIPTION OF THE INVENTION

The essential as well as optional components are described below.

Rigid Silicone Polymer

The compositions of the present invention contain at least one rigid silicone polymer which when applied to hair imparts style retention benefits.

The polymers comprise from about 0.01% to about 10% of the composition, preferably from about 0.05% to about 7%.

Polymers useful in the present invention include, but are not limited to, filler reinforced polydimethyl siloxane gums including those having end groups such as hydroxyl and resin reinforced siloxanes.

The rigid silicone polymers useful in the present invention have complex viscosities of at least $2 \times 10^5$ poise (P), preferably about $1 \times 10^7$ or more, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

A preferred siloxane gum is a diphenyl-dimethyl polysiloxane gum useful in the invention has a molecular weight of at least about 500,000, and must be diphenyl substituted to the extent of 3% or more, preferably at least about 5%. The siloxane gums are filler reinforced to provide additional rigidity. Silica is the preferred filler and is used at a level of from about 0.02% to about 2.00%.

Silicone resins are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in toluene which is stripped prior to the resin's use.

Surfactant For Premixing With Rigid Silicone

The surfactant used in the present invention to premix with the rigid silicone is an alkyl glyceryl sulfonate. This material, used at a level of from about 0.2% to about 12% of an aqueous paste containing about 50% water, provides for the rigid silicone to be dispersed into small droplets and distribute better onto the hair. The alkyl group associated with the surfactant generally has from about 10 to about 20 carbon atoms, preferably from about 12 to about 14.

Volatile Carrier

The compositions of the invention comprise a volatile carrier, or mixtures thereof, which preferably is present from about 0.1% to about 10%. The term "volatile" as used herein means that the material has a measurable vapor pressure.

Where the rigid silicone polymer is a polydimethyl siloxane or a polydiphenyldimethyl siloxane, the preferred carriers are volatile silicones having a boiling point between 99° C. to about 260° C. and have a solubility in water of less than about 0.1%. The degree of substitution on the siloxane (higher substitution, lower solubility) obviously affects the polymer's solubility and is taken into account by the formulator. The silicones may be either cyclic or linear polydimethyl siloxanes. The number of silicon atoms in the cyclic silicones is about 3 to about 7, most preferably 4 or 5. The general formula for the cyclic silicones is:

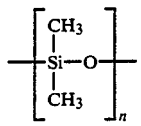

wherein $n=3-7$. Viscosities are generally less than 10 centipoise (cP) at 25° C.

Linear polydimethyl siloxanes useful in the invention generally have viscosities of less than about 5cP at 25° C. The linear volatile silicones contain from about 3 to about 9 silicone atoms and have the general formula $(CH_3)_3 Si-O-[Si (CH_3)_2O]_n Si (CH_3)_3$ wherein $n=1-7$.

Silicones of the above described types are widely available e.g., from Dow Corning as 344, 345 and 200 fluids; Union Carbide as Silicone 7202 and 7158, and Stauffer Chemical as SWS-03314.

Also useful in compositions of the invention are certain volatile hydrocarbons. These hydrocarbons may be either straight chain or branched, and contain from about 10 to about 16 carbon atoms, preferably from about 12 to about 16 carbon atoms.

Short chain alcohols such as ethanol are also suitable solvents for use in the present compositions.

Surfactants

The surfactants useful in the shampoo compositions of this invention can be present at a level of from about 10% to about 30%, most preferably from about 12% to about 25% of the composition. Surfactants useful in compositions of the invention include anionic, nonionic, cationic, zwitterionic and amphoteric surfactants.

Synthetic anionic detergents useful herein, particularly for the shampoo compositions, include alkyl and alkyl ether sulfates. These materials have the respective formulae $ROSO_3M$ and $RO(C_2H_4O)_xSO_3M$ where R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Another suitable class of anionic surfactants are the watersoluble salts of the organic, sulfuric acid reaction products of the general formula:

$R_1-SO_3-M$ wherein $R_1$ is chosen from the group consisting of a straight or branched chain, saturated aliphatic hydrocarbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$- n-paraffins.

Additional examples of anionic synthetic detergents which come within the terms of the present invention are the reaction products of fatty acids esterified with isethionic acid and neutralized with sodium hydroxide where, for example, the fatty acids are derived from coconut oil; sodium or potassium salts of fatty acid amines of methyl tauride in which the fatty acids, or example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate; tetrasodium N-(1,2-dicarboxyethyl)-N-octadecylsulfo-succinamate; diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued July 25, 1967, titled "Detergent Composition", the disclosure of which is incorporated herein by reference.

Another class of anionic organic detergents are the beta-alkyloxy alkane sulfonates. There compounds have the following formula:

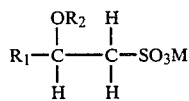

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include:

potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecylsulfonate, and ammonium β-n-propoxydodecylsulfonate.

Many additional nonsoap synthetic anionic surfactants are described in McCUTCHEON'S, DETERGENTS AND EMULSIFIERS, 1984 ANNUAL, published by Allured Publishing Corporation, which is incorporated herein by reference. Also, U.S. Pat. No. 3,929,678, to Laughlin et al., issued Dec. 30, 1975 discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrolphilic nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

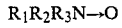

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethlyoctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dode-coxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxpyropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic surfactants, useful in shampoos, can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

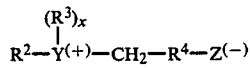

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate; p0 3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphate; and
5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the $RCONH(CH_2)_3$ radical is attached to the nitrogen atom of the betaine are also useful in this invention. The amido betaines are preferred for use in some of the compositions of this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. The alkyl sulfates, the ethoxylated alkyl sulfates and mixtures thereof are preferred for use herein.

Water

Water is the last essential component of the present invention's compositions and generally comprises from about 40% to about 90% of the total composition.

Optional Components

The present shampoo compositions herein can contain a variety of other optional components suitable for rendering such compositions more acceptable. Such conventional optional ingredients are well known to those skilled in the art, e.g., pearlescent aids such as ethylene glycol distearate; preservatives such as benzyl alcohol, ethyl paraben, propyl paraben and imidazolidinyl urea; thickeners and viscosity modifiers such as a diethanolamide of a long chain fatty acid (e.g., PEG 3 lauric diethanolamide), cocomonoethanol amide, dimethicone copolyols, guar gum, methyl cellulose starches and starch derivatives, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc.; coloring agents such as any of the FD&C or D&C dyes; hair oxidizing (bleaching) agents such as hydrogen peroxide, perborate and persulfate salts; hair reducing agents such as the thioglycolates; perfumes; and, sequestering agents such as disodium ethylenediamine tetraacetate, polymer plasticizing agents such as glycerin and propylene glycol. Such agents generally are used individually at a level of from about 0.01% to about 10%, preferably from about 0.05% to about 5.0% by weight of the composition.

The pH of the present compositions is not critical and may be in the range of from about 3 to about 10.

As with all compositions, the present compositions should not contain components which unduly interfere with the performance of the compositions.

METHOD OF MANUFACTURE

Methods of manufacture of the present shampoo compositions are described in the following examples.

INDUSTRIAL APPLICABILITY

The present compositions are used in a conventional manner.

The following Examples further illustrate the preferred embodiments within the scope of the present invention. The Examples are given solely for the purposes of illustration and are not to be construed as limitations of the present invention as many variations of the invention are possible without departing from its spirit and scope.

EXAMPLES I-IV

The following examples are representative of the present invention.

| Component | Weight % | | | |
|---|---|---|---|---|
| | I | II | III | IV |
| Ammonium Lauryl Sulfate | 12.810 | 12.810 | 14.000 | 13.500 |
| Ammonium Laureth Sulfate | 9.095 | 9.095 | 0.000 | 4.000 |
| Alkyl Glycereth Sulfonate | 1.256 | 2.512 | 9.000 | 2.177 |
| Ammonium Xylene Sulfonate | 0.010 | 0.000 | 0.000 | 0.750 |
| Dimethicone Gum*[1] | 1.000 | 2.000 | 4.500 | 2.000 |
| Silica[2] | 0.128 | 0.256 | 1.125 | 0.353 |
| Cyclomethicone | 1.000 | 2.000 | 4.500 | 2.000 |
| Coco Diethanol Amide | 2.300 | 2.300 | 0.000 | 0.000 |
| EDTA | 0.100 | 0.100 | 0.000 | 0.000 |
| Monosodium Phosphate | 0.500 | 0.500 | 0.000 | 0.000 |
| Disodium Phosphate | 0.380 | 0.380 | 0.000 | 0.000 |
| Salt | 2.000 | 2.500 | 0.000 | 0.000 |
| Perfume | 0.500 | 0.500 | 1.200 | 1.200 |
| Preservative | 0.033 | 0.033 | 0.033 | 0.033 |
| Coco Monoethanol Amide | 0.000 | 0.000 | 3.000 | 4.000 |
| Ethylene Glycol Stearate | 0.000 | 0.000 | 2.000 | 2.000 |
| Cetearyl Alcohol | 0.000 | 0.000 | 0.600 | 1.000 |
| Sodium Citrate | 0.000 | 0.000 | 0.050 | 0.050 |
| Citric Acid | 0.000 | 0.000 | 0.050 | 0.050 |
| Sodium Hydroxide | 0.000 | 0.000 | 0.010 | 0.027 |
| Sodium Chloride | 0.000 | 0.000 | 1.700 | 1.000 |
| Water | Q.S. | Q.S. | Q.S. | Q.S. |

[1]SE-30 or SE-76 Gum, General Electric
[2]Cab-o-sil HS-5, Cabot Corporation

The alkyl glycereth sulfonate (AGS) paste and rigid silicone/silica blend are mixed together at high shear in a ribbon mixer or comparable agitator for about 1-5 hours. At the end of this step, the mixture is a thick surfactant paste premix with finely dispersed silicone particles throughout the blend.

The paste premix is diluted with the water or surfactant solution diluent to form a lower viscosity silicone premix. This dilution takes place by mixing the materials with a ribbon mixer, agitator, blender, or other common mixing equipment. The concentration of the paste premix in the water or diluent can be from about 10 to about 90% of the total mix.

The diluted silicone premix can be added to an anionic surfactant shampoo base formula to disperse the silicones in a product base. This addition occurs at low to moderate agitation between about 70° and about 160° F.

The above described compositions all provide excellent hair condition and hair styling properties.

What is claimed is:

1. A shampoo composition comprising:
   (a) from about 0.01% to about 10% of a rigid silicone having a complex viscosity of at least $2 \times 10^5$ poise selected from the group consisting of filler reinforced polydimethyl siloxane gums, silicone resin reinforced silicone gums and mixtures thereof;
   (b) from about 10% to about 30% of a synthetic surfactant;
   (c) from about 0.1% to about 10% of a volatile solvent;
   (d) from about 0.2% to about 12% of about a 50% aqueous solution of an alkyl glyceryl sulfonate; and
   (e) the balance water, wherein a premix consisting of the rigid silicone and the alkyl glyceryl sulfonate is formed prior to mixing with the other shampoo components.

2. A shampoo composition according to claim 1 wherein the surfactant is selected from the group consisting of anionic, nonionic, amphoteric and zwitterionic surfactants and mixtures thereof.

3. A shampoo composition according to claim 2 wherein the rigid silicone is a filler reinforced polydimethyl siloxane gum.

4. A shampoo composition according to claim 3 wherein the volatile solvent is a volatile silicone.

5. A shampoo composition according to claim 4 wherein the filler material is a silica which is present at a level of from about 0.02% to about 2.00%.

6. A shampoo composition according to claim 5 wherein the surfactant is anionic.

7. A shampoo composition according to claim 6 wherein the surfactant is a mixture ammonium lauryl sulfate and ammonium laureth sulfate.

* * * * *